(12) United States Patent
Furumoto

(10) Patent No.: US 6,547,781 B1
(45) Date of Patent: *Apr. 15, 2003

(54) ULTRA-LONG FLASHLAMP-EXCITED PULSE DYE LASER FOR THERAPY AND METHOD THEREFOR

(75) Inventor: Horace W. Furumoto, Wellesley, MA (US)

(73) Assignee: Cynsure, Inc., Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/501,450

(22) Filed: Feb. 10, 2000

Related U.S. Application Data

(63) Continuation-in-part of application No. 08/835,012, filed on Apr. 8, 1997, now Pat. No. 6,273,883, which is a continuation of application No. PCT/US97/05560, filed on Apr. 4, 1997.
(60) Provisional application No. 60/015,082, filed on Apr. 9, 1996.

(51) Int. Cl.[7] .............................................. A61B 18/20
(52) U.S. Cl. ............................... 606/12; 606/9; 606/13; 607/89; 607/90
(58) Field of Search ..................... 606/3, 9–18; 607/88, 607/89, 90; 372/25–28

(56) References Cited

U.S. PATENT DOCUMENTS

| | | | | |
|---|---|---|---|---|
| 4,860,303 A | * | 8/1989 | Russell ........................ | 372/54 |
| 5,312,396 A | * | 5/1994 | Feld et al. .................... | 606/3 |
| 5,749,868 A | * | 5/1998 | Furumoto ..................... | 606/9 |
| 5,843,072 A | * | 12/1998 | Furumoto et al. ............. | 606/9 |
| 5,871,479 A | * | 2/1999 | Furumoto et al. ............. | 606/9 |
| 6,045,548 A | * | 4/2000 | Furumotor et al. ........... | 606/9 |
| 6,050,990 A | | 4/2000 | Tankovich et al. ............ | 606/9 |
| 6,101,207 A | | 8/2000 | Ilorinne | |
| 6,228,075 B1 | * | 5/2001 | Furumoto ...................... | 606/9 |
| 6,273,883 B1 | * | 8/2001 | Furumoto ...................... | 606/9 |

OTHER PUBLICATIONS

"A Practical Guide for the PhotoDerm VL User", Energy Systems Corp., Haifa, Israel, (1995) Commercial Brochure 8 Pages.

* cited by examiner

*Primary Examiner*—David M. Shay
(74) *Attorney, Agent, or Firm*—Hamilton, Brook, Smith & Reynolds, P.C.

(57) ABSTRACT

A flashlamp-excited dye laser generating light pulses for therapy has a circulator which circulates a gain media through a dye cell. A controller coordinates operation by triggering flashlamps to excite the laser gain media while the circulator is circulating the gain media. This operation enables the effective generation of laser light pulses with a duration of at least one millisecond. The laser pulse is formed from many subpulses. If the flow velocity of dye solution is great enough such that the new solution enters the resonant cavity before the solutions in the cavity are substantially spent, subsequent subpulses are not quenched, enabling the generation of ultra-long effective pulses with high fluences. Specifically, longer effective pulses of up to 50 msec are attainable with energies of up to 50 Joules. These energies enable reasonable spot sizes, which makes the invention relevant to cutaneous as well as deep tissue therapy, for example.

19 Claims, 7 Drawing Sheets

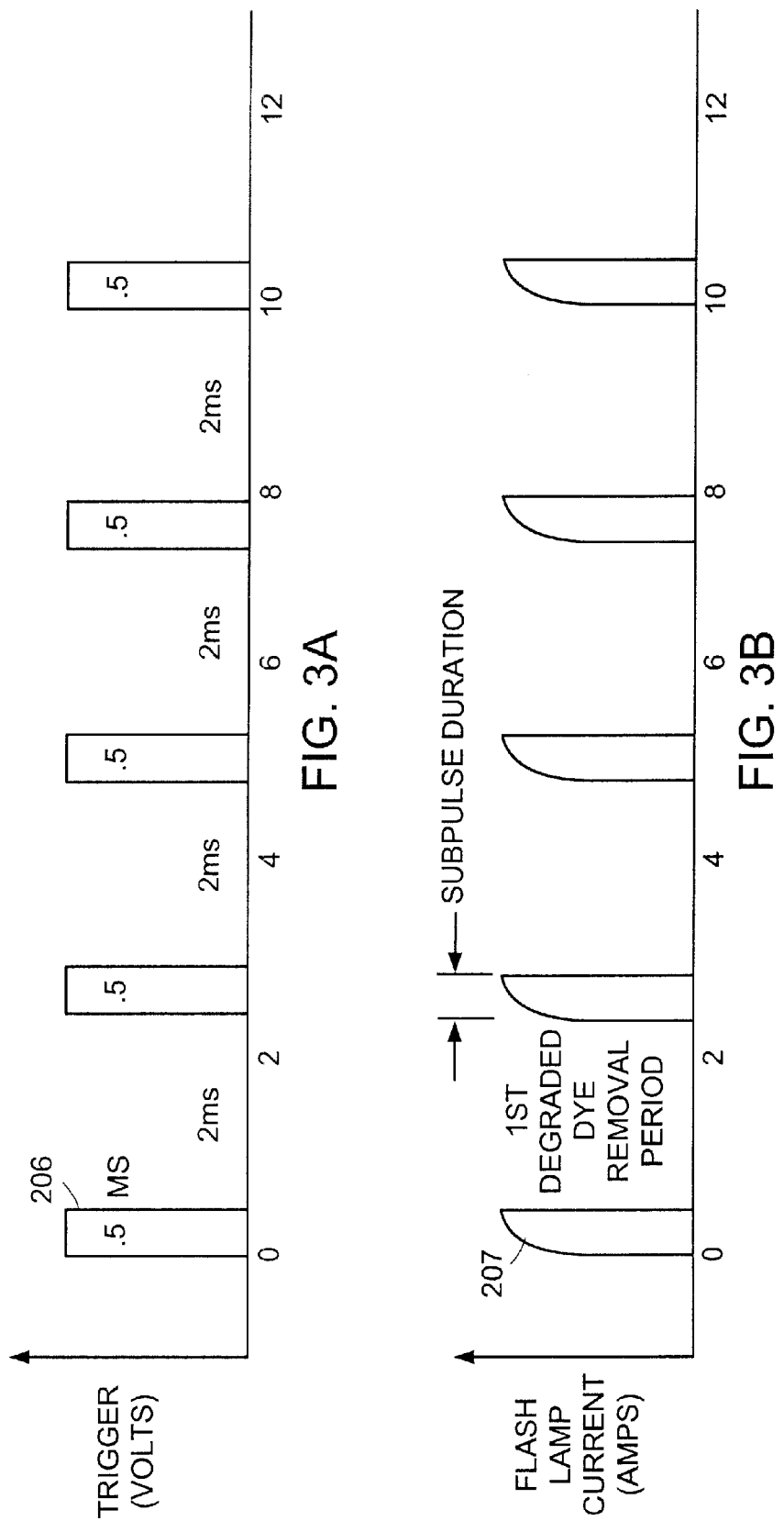

ULTRA-LONG FLASHLAMP-EXCITED PULSE DYE LASER FOR THERAPY AND METHOD THEREFOR

RELATED APPLICATIONS

This application is a continuation-in-part of U.S. patent application Ser. No. 08/835,012, filed Apr. 8, 1997, now U.S. Pat. No. 6,273,883 entitled "Alexandrite Laser System for Treatment of Dermatological Specimens," by Horace Furumoto, et al., which is a continuation of International Application No. PCT/US97/05560, filed Apr. 4, 1997, which claims the benefit of U.S. Provisional Patent Application Serial No. 60/015,082, filed Apr. 9, 1996, the entire teachings of which are incorporated herein by reference.

BACKGROUND OF THE INVENTION

Vascular lesions, comprising enlarged or ectatic blood vessels, pigmented lesions, and tattoos have been successfully treated with lasers for many years. In the process called selective photothermolysis, the targeted structure, the lesion tissue or tattoo pigment particles, and the surrounding tissue are collectively irradiated with laser light. The wavelength or color of this laser light, however, is chosen so that its energy is preferentially absorbed by the target. Localized heating of the target resulting from the preferential absorption leads to its destruction.

Most commonly in the context of vascular lesions, such as portwine stains for example, hemoglobin of red blood cells within the ectatic blood vessels serves as the laser light absorber, i.e., the chromophore. These cells absorb the energy of the laser light and transfer this energy to the surrounding vessel as heat. If this occurs quickly and with enough energy, the vessel reaches a temperature to denature the constituents within the boundary of the vessel. The fluence, Joules per square centimeter, to reach the denaturation of a vessel and the contents is calculated to be that necessary to raise the temperature of the targeted volume within the vessel to about 70° C. before a significant portion of the absorbed laser energy can diffuse out of the vessel. The fluence must, however, be limited so that the tissue surrounding the vessel is not also denatured.

As suggested, simply selecting the necessary fluence is not enough. The intensity and pulse duration of the laser light must also be optimized for selectivity by both minimizing diffusion into the surrounding tissue during the pulse while avoiding localized vaporization. Boiling and vaporization lead to mechanical, rather than chemical, damage—which can increase injury and hemorrhage in the tissues that surround the lesion. This constraint suggests that for the fluence necessary to denature the contents of the vessel, the pulse duration should be long and at a low intensity to avoid vaporization. It must also not be too long because of thermal diffusion, however. Energy from the laser light pulse must be deposited before heat dissipates into the tissue surrounding the vessel. The situation becomes more complex if the chromophore is the blood cell hemoglobin within the lesion blood vessels, since the vessels are an order of magnitude larger than the blood cells. Radiation must be added at low intensities so as to not vaporize the small cells, yet long enough to heat the blood vessels by thermal diffusion to the point of denaturation and then terminated before tissue surrounding the blood vessels is damaged.

Conventionally, flashlamp-excited dye lasers have been used as the laser light source. These lasers have the high spectral brightness required for selective photothermolysis and can be tuned to colors at which preferential absorption occurs. For example, wavelengths in the range of 577 to 585 nanometers (nm) match the alpha absorption band of hemoglobin and thus are absorbed well by the red blood cells in the blood vessels. The absorption of melanin, the principal pigment in the skin, is poor in this range, yielding the necessary selectivity.

Flashlamp-excited dye lasers, however, present problems in the pulse length obtainable by this type of laser. Theory dictates that the length of the light pulse should be on the order of the thermal relaxation time of the ectatic vessels or other dermal target. Ectatic vessels of greater than 30 microns in diameter are characteristic of cutaneous vascular lesions. These large vessels have relaxation times of 0.5 milliseconds (msec) and longer and thus require pulse durations of this length. Commercially available flashlamp-excited dye lasers generally have maximum pulse lengths that are shorter than 0.5 msec. Brute force excitation of the dye gain medium can result in pulses as long as 1.5 milliseconds. As a result, selective photothermolysis treatment of ectatic vessels larger than 30 microns currently relies on higher than optimum irradiance to compensate for the pulse duration limitations. This leads to temporary discoloration of the skin, viz., purpura.

With shorter than desirable pulse durations, purpura, which is a bluish lesion that appears as black and blue spots, forms at the treated site. It is not medically harmful nor is it permanent, and lasts but a couple of weeks. Patients prefer not to have this cosmetically undesirable side effect. It is commonly believed that pulses longer than 5 msec will reduce the formation of purpura.

Dierickx, et al., "Thermal Relaxation of Port Wine Stain Vessels Probed In-Vivo: The Need for 1–10 Millisecond Laser Pulse Treatments," *J. of Investigative Dermatology*, 105, 709–714, (1995) report the data and histologic assessment of the vessel injury strongly suggest that pulse durations for ideal laser treatment are in the 1–10 millisecond region and depend on vessel diameter. No dermatologic laser presently used for port wine stain treatment operates in this pulse width domain. Commercial medical dye lasers with pulse durations of 1.5 msec are now available but these lasers do not show the needed improvement in the treatment of ectatic vessels. Moreover, the combination of two dye lasers was suggested to generate 4.5 msec pulses according to U.S. Pat. No. 5,746,735 and the output used in leg vein treatment. The results showed marginal improvement over pulses 1.5 msec long. See Alora M. B., et al., "Comparison of the 595 nm Long Pulse (1.5 ms) and 595 nm Ultra Long Pulse (4 ms) Laser in Treatment of Leg Veins," American Society Laser Medicine 18th Annual Meeting Supplement 10, No. 158, (1998). It is therefore desirable to get to 10 msec and longer.

In dye lasers, it has been observed that the premature cessation of the lasing is caused primarily by the degradation of the dye solution. Improved dye solution_ formulations can yield some increases in pulse duration. Dye degradation, however, cannot be totally eliminated and other steps must be taken if pulse durations of 5 msec and longer and having the fluences for medical procedures are to be achieved.

One attempt at lengthening the pulse du ration utilizes a flashlamp-excited dye lasers that has a dye cell that permits rapid dye solution interchange during the laser excitation pulse. Specifically, the dye in the dye cell is replaced while the flashlamps are fired so that exhausted and degraded dye medium is removed from the resonant cavity and replaced with fresh dye medium during the excitation pulse, thereby facilitating the lengthening of the laser pulse. The approach is similar to that used to generate laser emission in cw dye lasers, albeit at the much higher energies required for these medical applications.

SUMMARY OF THE INVENTION

The batch replacement of dye solution and subsequent processing of the dye solution to lengthen the pulse duration in dye lasers has met with some success. Nonetheless, still longer pulses are required in some cases than currently appear practical using this technique.

The problem that appears to limit the practicality of this technique concerns the fact that it suboptimally uses the flashlamps. The low peak current may not be high enough to excite the dye gain medium well above threshold and the current below threshold is wasted making the long continuous pulse dye laser very inefficient. A preferred mode of operation for the dye laser to generate long, effective laser pulses is to use a sequence of short on and off flashlamp pulses. To generate long laser pulses without exceeding the explosion point of the flashlamp, the current through the lamp is limited to run safely without damaging the lamp. The short current pulses have peak currents that are well above the lasing threshold. The pulse duration of the individual pulse is short enough so as to be well below the explosion point of the flashlamp. If the time when the flashlamp is on and when it is off is shorter than the thermal relaxation time of the target to be heated, the heating effect is nearly the same as if the flashlamp was continuously on.

The above technique allows heating of a target by a sequence of on/off or pulse periodic pulses to be nearly the same as if the flashlamp is continually on, but does not compensate for loss of efficiency caused by degradation of the dye gain medium. But if the dye gain medium that is degraded by the excitation pulse could be extracted from the active gain volume before the next excitation pulse arrives, the dye gain medium will be fresh and not contain degraded dye solution that lessens the gain of the laser. Efficiency of the laser is therefore doubly enhanced by periodic pulsing, first by having flashlamp excitation pulse that is well above threshold, and secondly by removal of degraded gain dye solution when the flashlamp is not excited.

Consequently, the present invention is directed to a technique for generating long effective pulses. The degraded dye is removed during the long effective pulse. However, pulse periodic heating technique is used to preserve the flashlamps. The long effective pulse is optimal for therapeutic treatment, such as selective photothermolysis. This long effective pulse is comprised of much shorter subpulses across the duration of the effective pulse. The flashlamps are fired for only these short, but relatively intense pulses. In this way, the flashlamp useful life is preserved, since the flashlamp will be driven for only a few milliseconds to as short at microseconds. Moreover, overall pumping efficiency is improved since a greater percentage of the generated light is above the lasing threshold for the dye.

In some ways, this operation of a flashlamp-excited dye laser is similar to that used previously in isotope separation. Very high power laser beams were generated using very intense, but short, flashlamp pulses, in which the dye media was replaced.

The difference, relative to the present invention,, is that a pre-defined number of subpulses are created to yield a carefully controlled effective pulse duration that will be therapeutically efficacious. In contrast, the dye lasers used for isotope separation, operated essentially continuously with flashlamps pulsing at a rate of 100 to 1000 pulses per second. Moreover, in the present invention, the heating effect of the subpulse is cumulative on the target, and the total fluence of the effective laser pulse can be carefully controlled to maximize damage to the targeted structure, while minimizing collateral damage. In contrast, in isotope separation, each pulse of the train of pulses acted on new target material and the desired result for the isotope separation process will be degraded if the target material was irradiated more than once.

The pulse periodic operation is achieved by repeatedly triggering the flashlamp(s) while a dye solution is being circulated through the resonant cavity of the laser, typically a dye cell. If the flow velocity of dye solution is great enough, such that the new solution enters the cavity, and the next flashlamp subpulse excites the new fresh dye gain medium, ultra-long-effective pulses with high fluences are possible. Specifically, longer effective pulse duration of up to 50 msec, and longer, can be achieved with energies of up to 50–100 Joules, and greater. These high energies enable treatment with reasonable spot sizes, which makes the invention relevant to medical therapy.

According to one aspect, the invention features a flashlamp-excited dye laser generating light pulses at a color and pulse duration required for selective photothermolysis. This laser preferably comprises a cell containing a laser gain media located in a resonant cavity. Dye solutions are typical examples of such gain media. At least one flashlamp is provided to excite the gain media in the cavity, typically contained in the cell. A circulator is used to circulate the gain media through the cavity. Finally, a controller coordinates operation by triggering the flashlamp to excite the laser gain media, while the circulator is circulating the gain media through the cell. Laser light subpulses are generated with a duration of a few hundred microseconds with a low energy content so as not to create unwanted side effects such as purpura. Though each subpulse has low energy, the thermal effect of the subpulses are cumulative, and the heating effect of the long effective laser pulse is about the same as if the effective laser pulse was on continuously.

For some applications, the effective duration of the output laser light pulse containing the subpulses is preferably at least five milliseconds. Generally, the cumulative energy of the subpulses is about twenty Joules, but can be as large as 50 Joules, which may be necessary for large targets.

In specific embodiments, the circulator replaces gain media in the dye cell with new gain media between the generation of subpulses so that enough new gain media is within the cell to enable the generation of the subsequent subpulse. This operation ensures that the laser output will not be quenched by accumulation of exhausted dye solutions.

Different configurations for the gain media flow through the dye cell can be implemented. In one embodiment, the flow is transverse to the laser axis; in another, the flow is longitudinal, or parallel, to the axis. Preferably, if the longitudinal configurations are implemented, a plurality of media input ports are provided along the cell. A plurality of media output ports are also useful to allow flow out of the cell. The dye cell segments between the adjacent inlet and outlet ports is ideally short so that the residence time of the flowing gain media through the dye cell segment is less than the period between subpulses.

In the transverse flow embodiment, the gain media flows between two parallel or nearly parallel transparent cell walls, which allows the excitation light to enter the dye cell. The transparent cell walls are long in the direction of the flashlamps and laser resonator axis and shorter in the direction of the flow. The gain media flows perpendicular to the long axis of the dye cell and is contained within allow excitation light from the flashlamp to enter the dye cell and within another set of allow the laser light to reflect between mirrors that comprise the laser resonator.

According to another aspect, the invention can also be characterized in the context of a method of operation for a flashlamp-excited dye laser. Such a method comprises exciting the dye solution in the resonant cavity with a flashlamp and then generating a laser light output subpulse from the resonant cavity with the excited dye solution. The excitation at least partially exhausts the dye solution. To counteract this effect, some of the at least partially exhausted dye solution is replaced in the resonant cavity with new dye solution before the generation of the next subpulse, within the duration of the longer effective pulse. The number and cumulative fluence of the subpulses is defined such that the effective pulse duration is appropriate to treat the targeted tissue, while minimizing the detrimental impact on the matrix surrounding the targeted structures.

The above and other features of the invention including various novel details of construction and combinations of parts, and other advantages, will now be more particularly described with reference to the accompanying drawings and pointed out in the claims. It will be understood that the particular method and device embodying the invention is shown by way of illustration and not as a limitation of the invention. The principles and features of this invention may be employed in various and numerous embodiments without the departing from the scope of the invention.

BRIEF DESCRIPTION OF THE DRAWINGS

In the accompanying drawings, like reference characters refer to the same parts throughout the different views. The drawings are not necessarily to scale, emphasis instead being placed upon illustrating the principles of the invention. Of the drawings:

FIGS. 3A, 3B, 3C, and 3D are a timing diagrams showing the relationship between the trigger signal from the controller 160, the flashlamp driving current, the laser pulse amplitude of the dye laser, the tissue heating effect of the subpulses.

DETAILED DESCRIPTION OF THE INVENTION

Figure 1:
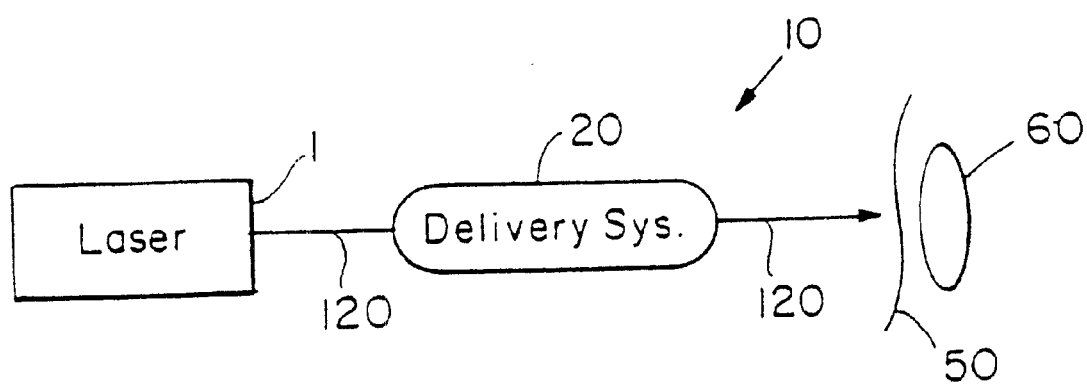
FIG. 1 schematically shows a selective photothermolysis treatment system of the invention.

Turning now to the drawings, FIG. 1 shows a selective photothermolysis treatment system 10, which has been constructed according to the principles of the present invention.

A flashlamp-excited pulse dye laser 1 for the system 10 generates an output laser light pulse 120. The output laser light pulse 120 is coupled into a medical delivery system 20, such as a single optical fiber, and transported to the skin 50 or other tissue of a patient. The output laser light pulse 120 achieves substantial penetration to treat the targeted dermal structure 60, such as a vascular lesion.

The targeted structure 60 is one of many different types of lesion, depending on the application, such as portwine stain birthmarks, hemangiomas, telangiectasia, idiopathic vulvodynia, and leg veins. Further, the targeted structures, in other applications, are vessels in simple wrinkles, caused by age or sun exposure, blood vessels in scar tissue, or hair follicles. In this last application, the target is thepapilla, which the pulse permanently damages in order to yield permanent or semi permanent hair removal in a region of the patient's dermis.

The effective pulse duration of the output laser light pulse 120 are matched to the thermal relaxation time of the targeted structure. Generally, this requires durations greater than 0.2 msec. For vessels of 30 microns in diameter and larger, as are present in portwine stains of adult patients, the duration should ideally exceed 0.5 msec, whereas pulse durations of 1 msec to 10 msec or longer to 20–30 msec should be selected when the vessels are larger than 100 microns or for hair removal applications.

Figure 2:
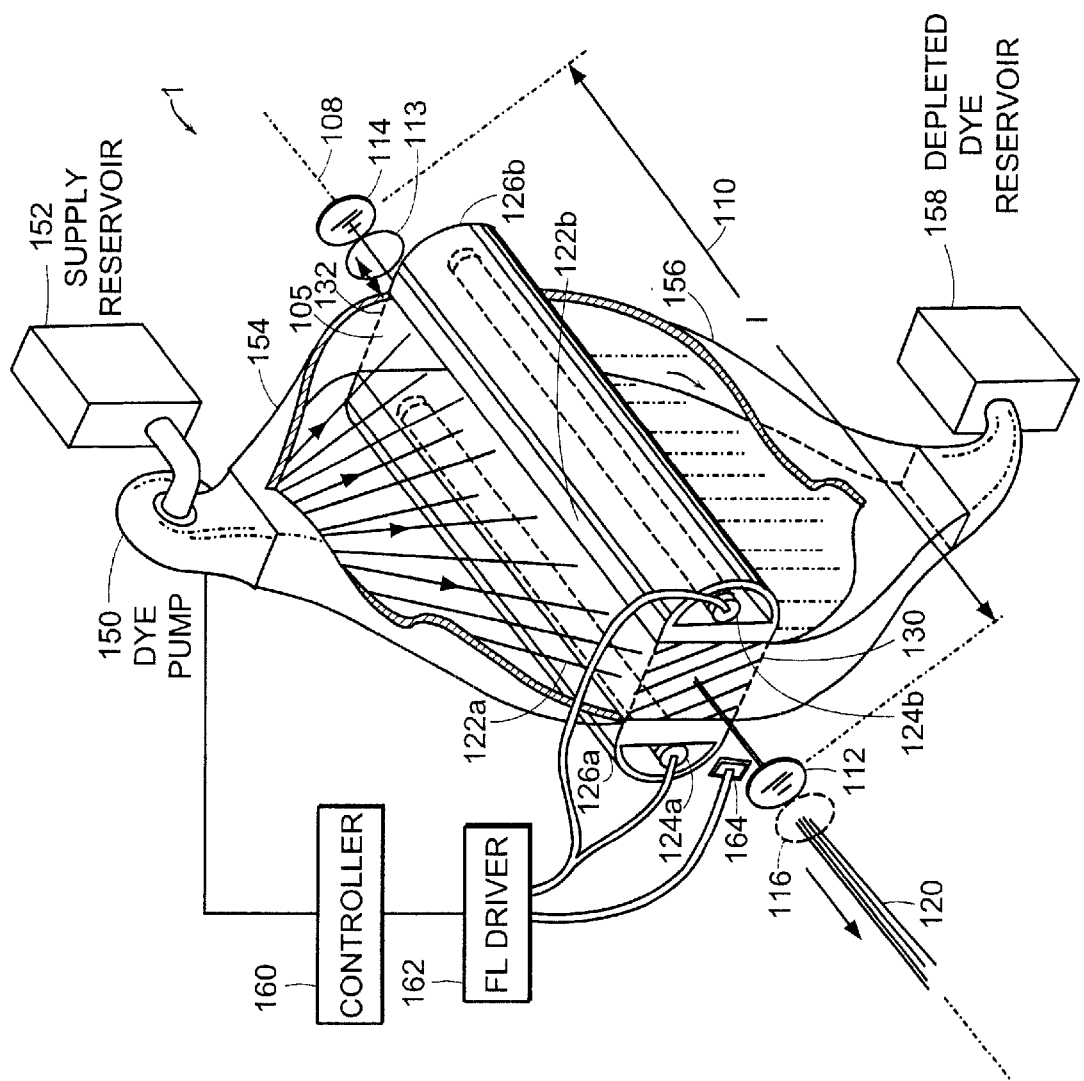
FIG. 2 is a schematic perspective view of a first embodiment of the flashlamp-excited pulse dye laser 1 of the present invention.
Figure 3C:
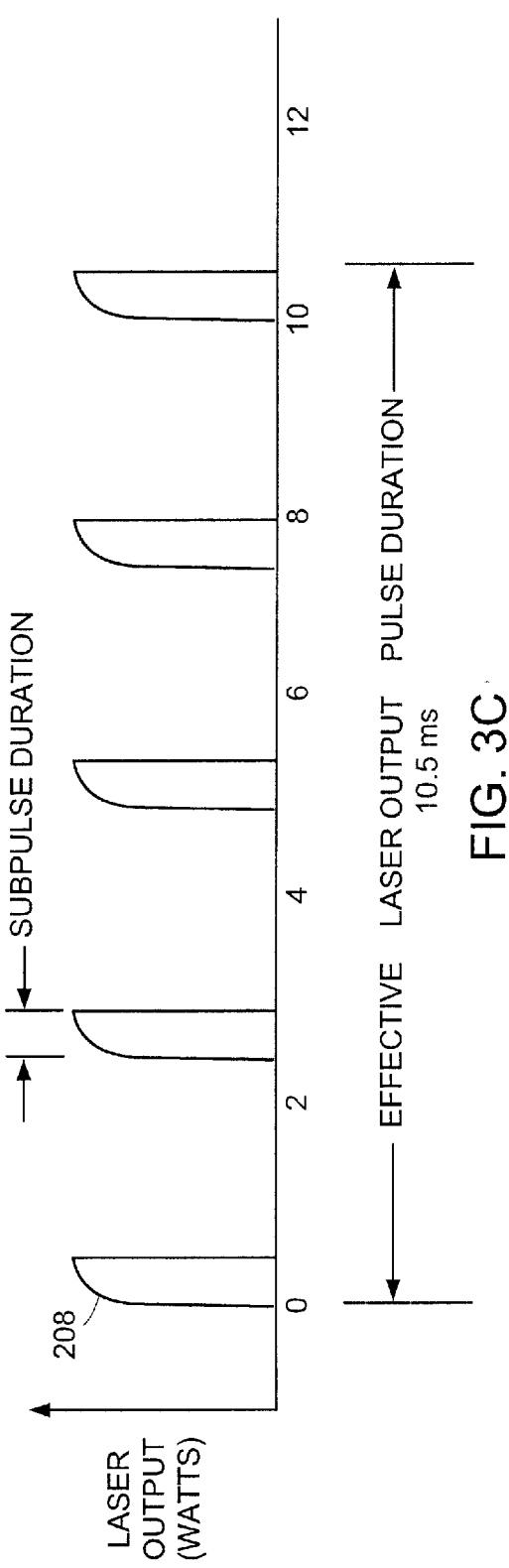
Figure 3D:
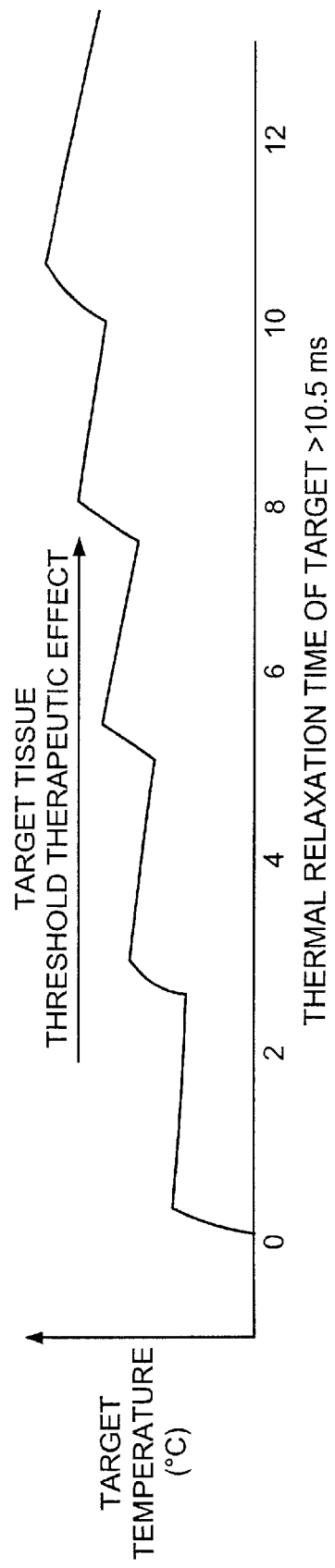

FIG. 2 is a schematic diagram illustrating the flashlamp-excited pulse dye laser 1 in more detail. As is generally common among most such lasers, a dye cell 105 for containing a liquid laser gain media, specifically a dye solution, extends longitudinally along a center axis 108 of the laser 1. A front window 130 and a rear window 132 define the longitudinal extent of the dye cell 105. Both windows 130 and 132 are transparent. The dye cell 105 is located in a resonant cavity 110, the ends of which are defined by a first mirror 112 and a second mirror 114. A tuning element 113, typically a birefringent filter, allows selection of the appropriate wavelength for therapeutic or cosmetic treatment. Usually, the cavity supports multiple spatial and longitudinal modes, to yield a top-hat output beam spatial profile, instead of a more Gaussian distribution.

While the second mirror 114 is fully reflective, the first mirror 112 is partially reflective and partially transmissive, defining an output aperture 116. As a result, a portion of the light generated in the resonant cavity 110 passes through this first mirror 112 as the output beam 120 of the laser 1.

The dye solution in the dye cell 105 is optically pumped by flashlamps 124a and 124b. Exterior to a light-transmissive left side wall 122a of the dye cell 105 is a left flashlamp 124b. A right flashlamp 124a is on an exterior side of a right side wall 122b, which is also transmissive to light. These flashlamps 124a, 124b generate broadband light that excites the dye solution contained in the dye cell 105. This results in the stimulated emission of light from the excited dye solution. Right and left reflectors 126a and 126b surround the respective flashlamps 124a and 124b to maximize the light injected into the dye cell 105. These reflectors are typically elliptical or diffuse.

The flashlamps 124a and 124b used in the present invention preferably have higher pulse energy capacity than typically found in short pulse dye lasers. During the generation of an output laser light pulse of 5 msecs, the total pumping energy injected into the dye solution by the flashlamps is approximately 2000 Joules.

A dye circulator functions to circulate dye solution through the dye cell 105.

Specifically, the dye circulator 150 circulates dye solution through the dye cell 105 such that subpulses are generated across the effective, operator-selected pulse duration. Typically, this is achieved by replacing enough of the dye solution between subpulses such that the lasing action will not be quenched in the subsequent subpulse to thereby allow its generation. Typically, the circulator circulates dye solution such that at least half of the dye solution is replaced within the period defined by the beginning of one subpulse to the beginning of the subsequent subpulse. Preferably, at least 90% of the dye solution is replaced between subpulses in one embodiment.

In the embodiment shown, this circulator includes a dye pump 150 which receives new dye solution from a supply reservoir 152. The dye is pumped into a supply manifold 154 (shown here in phantom), which distributes the dye solution flow along the longitudinal axis 108 of the dye laser 1. The dye solution flows through the dye cell 105, and thus the resonant cavity 110, in a direction transverse to the axis 108 of the laser 1. A collection manifold 156 (in phantom) collects the dye solution after it has passed through the dye cell 105 and directs it to a depleted dye reservoir 158.

A separate supply reservoir 152 and depleted dye reservoir 158 are not strictly necessary. Recirculation and filtration systems are possible. U.S. patent application Ser. No. 08/165,331, filed on Dec. 10, 1993, entitled Method and Apparatus for Replenishing Dye Solution in a Dye Laser, which is incorporated herein by this reference, is directed a system in which by-products from the lasing process are filtered out and the dye solution reused.

A controller 160 coordinates the operation of the dye pump 150 and the flashlamp driver 162. Specifically, in one embodiment, the system operator first selects a desired effective laser pulse duration. This determination is typically based on the observed size of the targeted structures. The controller then determines the number of flashlamp subpulses that are to be generated to achieve the selected laser pulse duration. Thereafter, the controller 160 first establishes a steady state flow of dye solution through the dye cell 105 by activating the dye pump 150. When the dye solution is flowing through the dye cell 105, the controller 160 then sends a trigger signals to a flashlamp driver 162 for each subpulse. The trigger signal defines the subpulse durations and causes the flashlamp driver 162 to supply a driving current to the flashlamps 124a and 124b. Light from the flashlamps excites the dye solution to lase and produce the output laser light 120 having the selected effect pulse duration.

Constant amplitude output laser light subpulses are produced with an intensity detector 164 that senses the intensity of the output laser light 120 and provides feedback to the flashlamp driver 162 in one embodiment. Typically, the detector is a diode or other photodetector that generates an intensity signal indicative of the amplitude of the output laser light. This signal is received by the flashlamp driver 162. There, the feedback signal is combined with the trigger signal. This allows the flashlamp driver to adaptively modify the level of the driving current to the flashlamps 124a, 124b in response to the instantaneous intensity of the output laser light. If the gain medium contains a dynamic concentration of depleted dye, a modulated excitation is required to maintain constant output. If depleted dye can be removed quickly, the excitation pulse will remain nearly constant, however.

Usually, some exhausted dye solution tends to accumulate in the dye cell 105 over the course of the long effective pulse. In fact, even with fast circulation, the percentage of new, unexhausted, dye is never as large as during the first subpulse. At least some of the light generated in the dye cell 105 is absorbed by this exhausted dye solution and this effect tends to increase the threshold level of excitation needed for subsequent subpulses. The intensity detector 164 detects any reduction in output light amplitude and causes the flashlamp to be driven harder to maintain constant output levels. Thus, the driving current is varied to maintain a constant amplitude series of subpulses in the output light amplitude.

The amount of dye degraded in each subpulse depends on the excitation energy level of the flashlamp subpulse. The higher the excitation energy, the more dye molecules are degraded. And, the amount of degraded dye left in the dye cell excitation volume before the next excitation subpulse depends on the flow velocity of the dye solution through the cell and length of the cell in the flow direction. Low viscosity solution such as those made from alcohol solvents can achieve velocities up to about 10 meters per sec with the use of a pump of practical size. With solvents such as ethylene glycol, often used because it is less of a fire hazard, flow velocities through the dye cell may be limited to 5 meters per second. In transverse flow flashlamp excited dye lasers, the height of the excitation zone parallel to the flow direction is limited by the height of the window or the image of the flashlamp if focusing specular reflectors are used to transfer light from the flashlamp to the dye cell. In either approach, the excitation zone height is about 1 cm. If the flow is 5 meters per second, the dye solution is interchanged in $\frac{1}{500}$ of a second using plug flow calculation. If the flashlamp light is off for 2 msec, one plug flow of degraded dye is removed before the next excitation pulse. If the thermal relaxation time of the target is much longer than 2 msec, successive subpulses will have a cumulative thermal effect on the target.

Photothermolysis treatment of larger ectatic vessels, for example, require the longer pulse durations obtainable by the present invention. Vessels of 100 and 200 micrometers in diameter have thermal relaxation times of 4.8 and 19.0 msec, respectively, and require similar pulse durations for optimally effective therapy. A flushing time of 2 msec is adequate to remove degraded dye for these size and larger blood vessels and still allow heating of the vessels by the cumulative effect of the subpulses. Energies required in the effective laser pulse to treat these size vessels are usually from 1 to 20 Joules, but fifty Joules may be required in hair removal applications.

FIGS. 3A–3D show trigger signal voltage, the flashlamp excitation current in Amperes, the laser pulse amplitude 120 as a function of time during the pulse generation, and the cumulative heating effect, respectively. Specifically, the controller 160 first engages the dye pump 150 to establish steady state dye flow through the dye cell 105 prior to the beginning of the laser pulse. The controller 160 then sends the first subpulse trigger signal 206. This yields the first flashlamp excitation current function 207 with capacitive and inductive distortion. The result is the first laser light sub-pulse 208. For simplicity, in this embodiment, the negative feedback constant intensity control is not activated and constant gate drive is used to control the switching transistors.

Thereafter, additional subpulse trigger signals are generated. In the specific embodiment, there are a total of five sub-pulse triggers, each being one half millisecond in length. There is a resting time of two milliseconds between each trigger signal. There are five on subpulses and four periods when the flashlamp(s) are off. As a result, the effective pulse duration is ten and one half milliseconds long. A feature of note, however, is the fact that this long effective pulse duration is obtained from a flashlamp with easily obtainable one half millisecond long subpulses.

Figure 4:
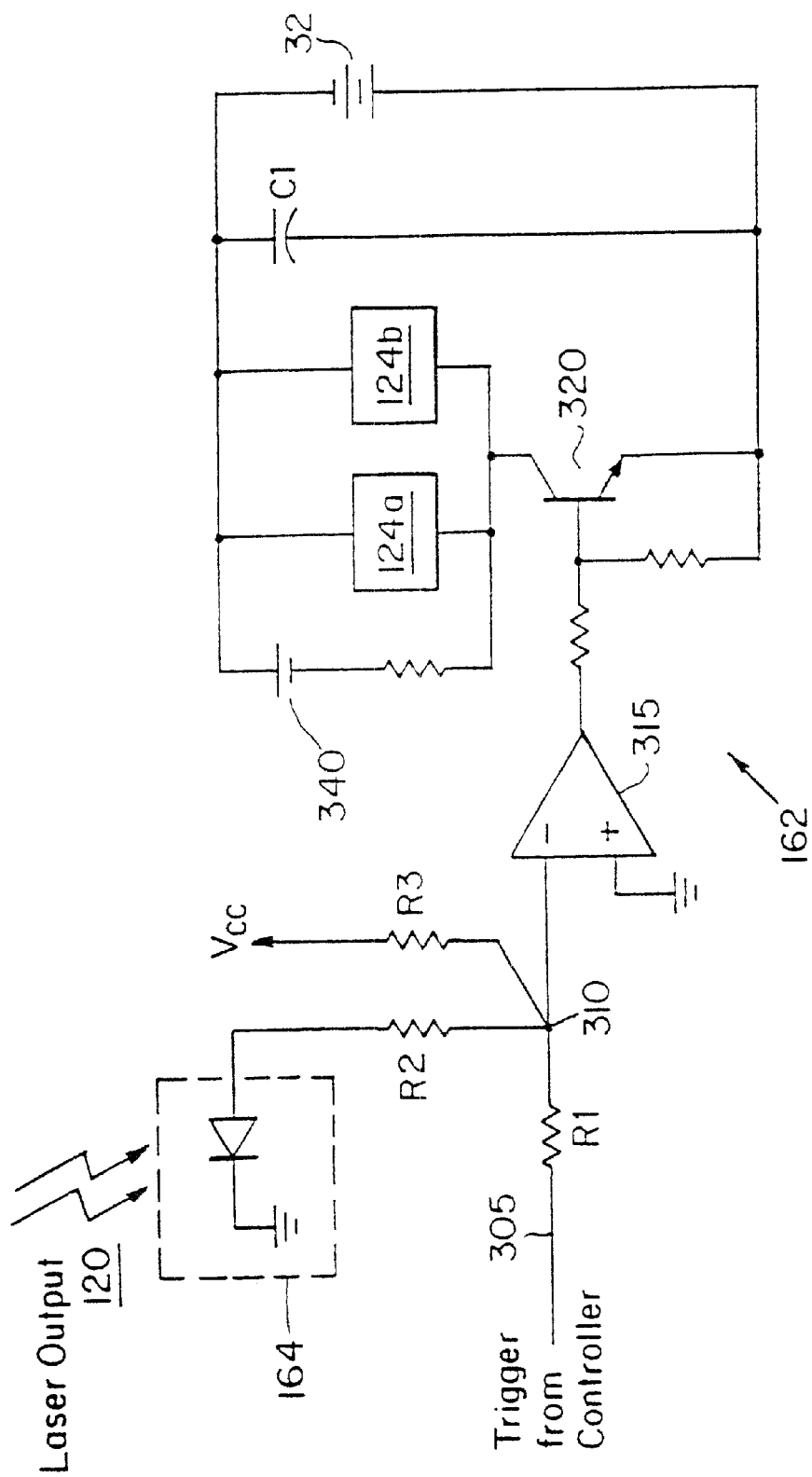
FIG. 4 is a circuit diagram of the flashlamp driver 162 of the present invention.

In another embodiment, FIG. 4 shows a circuit diagram of the flashlamp driver 162 shown in FIG. 2 that actively controls the level of driving of the flashlamps in response to the intensity of the generated laser light. Specifically, the flashlamp driver 162 receives the trigger signal from the controller 160 via conductor 305. This subpulse trigger signal defines the time for which the flashlamps will be driven for the subpulse. The length of the laser light pulse is tunable by changing the number of subpulse trigger signals generated, assuming a constant subpulse-to-subpulse period.

Specifically, in the typical application, the laser operator selects a desired pulse duration. Typically, the operator makes this decision based upon the specific application. For example, when small veins are the target, typically shorter pulse durations of 1–20 milliseconds are optimum. For very large ectatic vessels, pulse durations of 10–100 milliseconds may be necessary. When the target is the hair papilla, pulse durations of 10–50 milliseconds are preferred. In any case, the user enters the desired pulse duration.

The controller 160 then determines the subpulse duration. For example, in the illustrated example of FIG. 3A, 0.5 milliseconds subpulses are used. Typically, the subpulses must be long enough to not vaporize the chromophore. As a result, subpulses are typically longer than 0.1 milliseconds. With dye lasers, the subpulses, however, typically must be shorter than two milliseconds for efficient flashlamp operation and longevity. Then, the controller defines the time period between successive pulses. In the illustrated example of FIG. 3A, a resting time of two milliseconds is provided between each subpulse. As a general rule, the time between subpulses must be less than the thermal relaxation time of the targeted structure for selectivity. Finally, the controller determines the total number of subpulses across the effective pulse duration. Again, in the example illustrated in FIG. 3A, five subpulses are generated to yield an effective pulse duration of about 10.5 milliseconds. Longer effective pulse durations are obtained simply by programming a long pulse duration into the controller, which then simply generates a longer series of subpulses.

In the constant intensity mode of operation, the trigger signal is received at a summing node 310 through a resistor R1. The feedback signal, which is indicative of the intensity of the output laser light 120, is received from the intensity detector 164 through a resistor R2 also at the summing node 310. The voltage of the summing node is biased by third resistor R3 that is connected between the summing node 310 and the supply voltage Vcc. In the particular embodiment shown, the trigger signal is a low level active signal which pulls the voltage of the summing node 310 below ground. A comparator 315 compares the voltage of the summing node to the ground potential. Thus, in response to a receipt of the trigger signal the comparator 315 turns a power transistor such as an insulated gate breakdown transistor (IGBT) or power Darlington 320 on, rendering the transistor conductive. This event places the voltage of a high voltage power supply 325 across the flashlamp, which generates a driving current to the flashlamps 124a and 124b. A capacitor C1 stores charge to assist in driving the flashlamps 124a, 124b. A simmer supply 340 is also connected across the flashlamps 124a and 124b to provide a simmer current to maintain a stable voltage across the lamp prior to the main excitation pulse. Without the simmer, operation is erratic. This simmer current is evident from portion 205 of the flashlamp excitation plot in FIG. 3.

Figure 5A:
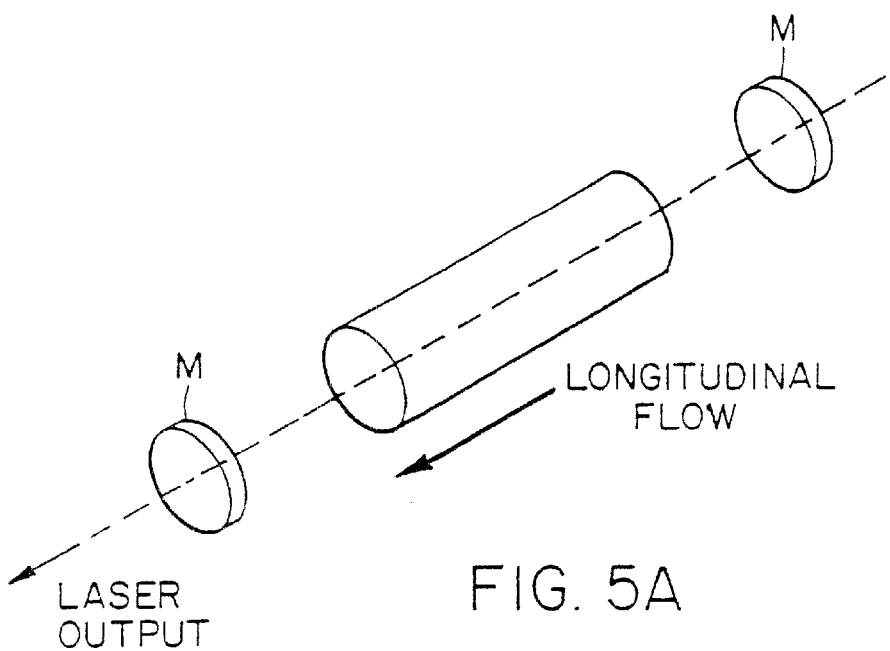
FIGS. 5A and 5B show the differences between longitudinal and transverse dye flow, respectively, through the resonant cavity of a laser.
Figure 5B:
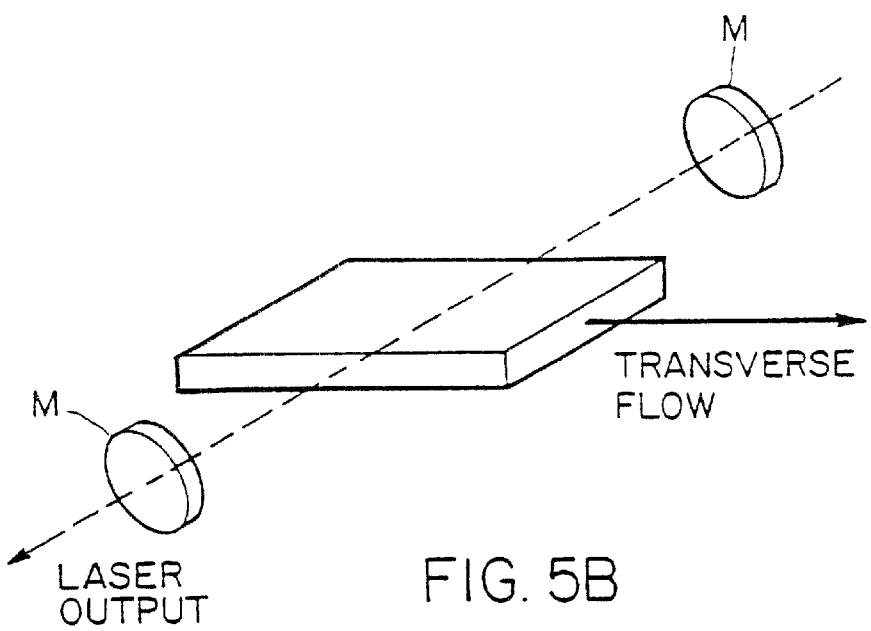

FIGS. 5A and 5B illustrate the differences between a longitudinal flow dye laser and the transverse flow configuration. The first embodiment of FIG. 1 corresponds to the transverse flow type of FIG. 5B. These configurations generally provide shorter residence time of the dye solution in the dye cell 105. The dye solution must merely move across the width of the resonant cavity 110. The longitudinal flow configuration of FIG. 5A offers an alternative. But, since the dye solution moves along the length of the dye cell, resident time is longer for the same flow velocity.

Figure 6:
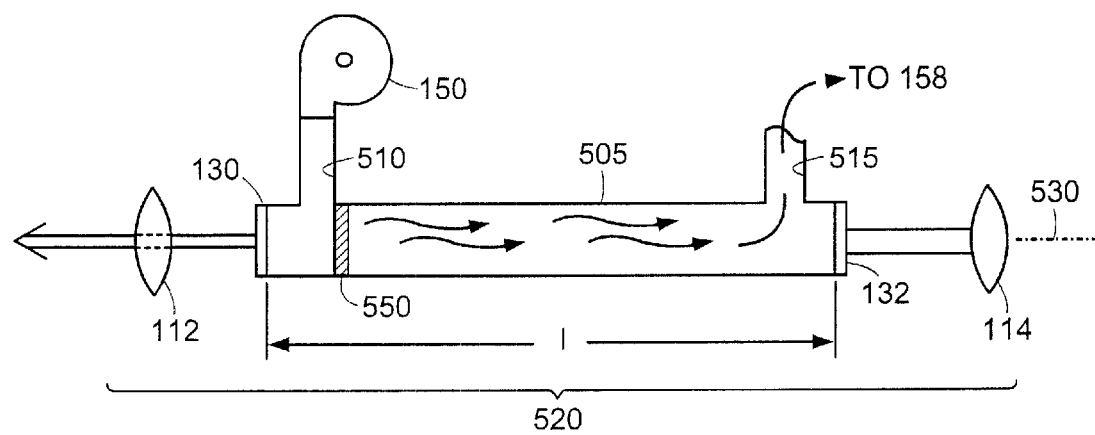
FIG. 6 schematically shows a dye cell 105 configured for longitudinal dye flow through the dye cell.

FIG. 6 illustrates a second embodiment of the dye cell 505 in which the dye solution travels longitudinally along the length of the dye cell 505, parallel to the laser axis 530. The dye solution is circulated through an input port 510 by a pump 150. The dye travels the length 1 of the dye cell 505 and exits an output port 515. First and second mirrors 112, 114 define the resonant cavity 520 in which the dye cell 505 is located as described in connection with FIG. 1.

The second embodiment configuration places certain limits on the dye cell 505 construction. A given cross-section of fluid 550 should traverse the length of the dye cell 505 in approximately 2.5 msec. This is a good estimate for the useable lifetime of dye solutions during lasing. But, velocity is limited by the pressure the dye cell 505 can withstand. A rule of thumb is that a flow of 10 meters per second is the maximum speed for pumps operating below 100 pound per square inch (psi) for alcohol solvent and 5 meters per second for ethylene glycol solvents. These factors limit the length of the dye cell 505 to approximately one half to one inch in length.

Figure 7:
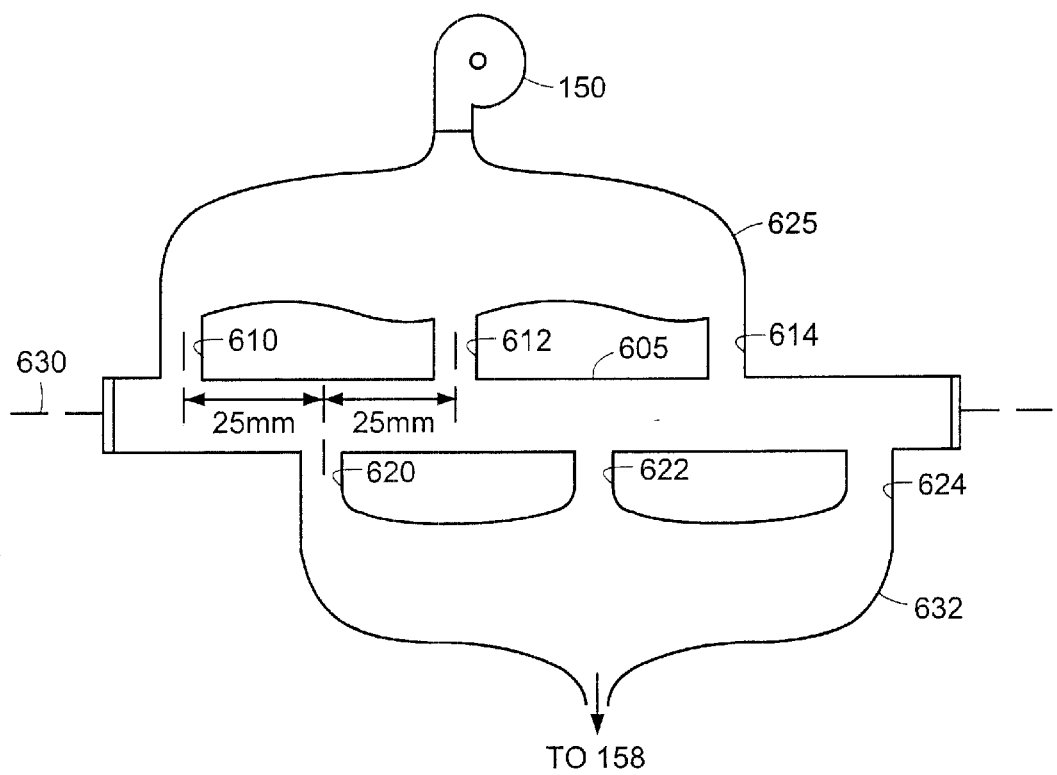
FIG. 7 schematically shows a dye cell 105 configured for longitudinal dye flow and having multiple input 610–614 and output ports 620–624 to reduce the residence time of dye solution in the dye cell 105.

FIG. 7 shows a third embodiment based upon a modification of the second embodiment of FIG. 6. Here, a plurality of dye input ports 610, 612, 614 are placed longitudinally along the length of dye cell 605. An input manifold 625 of the circulator supplies dye to each of these ports from a pump 650. Output ports 620, 622, 624 are placed between the input ports 610–614 on the opposite side of the dye cell 105. An output manifold 632 collects dye solution exiting the dye cell 605 through these ports. In this configuration, dye flowing through any one of the input ports 610–614 is divided and passes out both of the nearest output ports 620–624, again flowing parallel to the laser axis 630. If the longitudinal distance between an input port and the closest output port is approximately 25 mm, 50 mm between adjacent input ports, a flow velocity of 10 m per sec is sufficient to limit the residence time of the dye solution to 2.5 msec. This allows the dye solution to be interchanged twice in a 5 msec effective laser pulse duration or four times in a 10 msec effective pulse.

Dye lasers having a transverse flow of dye gain media through the resonant cavity have been developed in the past in a number of different contexts for different applications. Continuous wave (cw) dye lasers have even been developed. The dye in these lasers is pumped by another laser. This laser is focused on a small spot on a curtain of the flowing dye solution. Thus, volume of dye excited in this device is very small. Only the small portion of the dye curtain in the path of the beam from the focused pumping laser is excited, and therefore generates light by stimulated emission. Even though this type of laser-excited dye laser generates a continuous wave output, it can not produce the kilowatts of average power required by medical applications.

Very high pulse rate transverse flow dye lasers have been developed for isotope separation applications. The intent of these designs is to produce output energies of approximately one Joule in a few microseconds. Thermal distortion, which limited firing rates were avoided by replacing the excited dye in the resonant cavity from a previous pulse with new dye and then triggering the flashlamp. Such devices have been shown to generate pulse frequencies of almost one kilohertz. In these industrial applications, the peak and average output powers far exceed those required for medical procedures where longer pulse durations, moderate peak and average powers at lower frequencies are preferred. Average power close to a kilowatt has been generated using transverse flow dye lasers. For medical application, average power of at most a few tens of watts is required. Moreover, specifically defined effective pulse durations are a necessity.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A flashlamp-excited pulse dye laser system generating light pulses for therapy, comprising:

an optical system defining a resonant cavity and providing at least a portion of light generated in the resonant cavity as an output laser light pulse;

a cell for containing a laser gain media in the resonant cavity;

a flashlamp for exciting the laser gain media contained in the cell;

a circulator for circulating the laser gain media through the cell;

a controller for triggering the flashlamp to excite the laser gain media while the circulator is circulating the gain media through the cell to generate a long effective laser light pulse, comprising a series of shorter-duration subpulses, having duration of greater than one hundred microseconds; and a medical delivery system for transmitting the output laser light pulse to tissue of a patient.

2. A flashlamp-excited pulse dye laser, comprising:

an optical system defining a resonant cavity and providing at least a portion of light generated in the resonant cavity as an output laser light pulse;

a flashlamp for exciting the laser gain media contained in the cavity;

a circulator for circulating the gain media through the cavity; and a controller for triggering the flashlamp to excite the laser gain media while the circulator is circulating the gain media through the cavity to generate a long effective laser light pulse, comprising a series of shorter-duration subpulses, the long effective laser light pulse having a duration of greater than 0.1 milliseconds.

3. A flashlamp-excited pulse dye laser as described in claim 1, wherein the effective duration of the effective laser light pulse is at least five milliseconds.

4. A flashlamp-excited pulse dye laser as described in claim 1, wherein the energy of the effective laser light output pulse is less than 50 Joules.

5. A flashlamp-excited pulse dye laser as described in claim 1, wherein the controller triggers the flashlamp to initiate generation of at least two laser light subpulses pulses during the effective laser light pulse.

6. A flashlamp-excited pulse dye laser as described in claim 1, wherein the circulator circulates the gain media through the cell in a direction transverse to a longitudinal axis of the resonant cavity.

7. A flashlamp-excited pulse dye laser as described in claim 1, further comprising a medical delivery system for transmitting the output laser light pulse to a patient tissue.

8. A flashlamp-excited pulse dye laser as described in claim 1, wherein the circulator circulates the gain media through a cell in a direction parallel to a longitudinal axis of the resonant cavity.

9. A flashlamp-excited pulse dye laser as described in claim 8, wherein a plurality of media output ports are provided longitudinally along the cell, the media output ports enabling at least partially exhausted gain media to exit from the resonant cavity.

10. A flashlamp-excited pulse dye laser as described in claim 8, wherein a plurality of media input ports are provided longitudinally along the cell, the media input ports receiving the gain media from the circulator.

11. A flashlamp-excited pulse dye laser as described in claim 10, wherein a plurality of media output ports are provided longitudinally along the cell, the media output ports enabling at least partially exhausted gain media to exit from the resonant cavity.

12. A laser treatment method for treating biologic tissue of a patient, comprising:

operating a pulse dye laser to generate a long effective laser light output pulse having an effective pulse duration greater than 0.1 msec, the long effective laser light output pulse comprising a series of subpulses, and each subpulse having a shorter duration than the effective pulse duration; and delivering the long effective light output pulse to biologic tissue of a patient.

13. The method as described in claim 12, wherein the effective pulse duration is greater than 0.5 msec.

14. The method as described in claim 12, wherein the effective pulse duration is greater than 5 msec.

15. The method as described in claim 12, wherein the effective pulse duration is greater than 50 msec.

16. A method of operation for a flashlamp-excited pulse dye laser, the method comprising:

periodically exciting dye solution in a resonant cavity with a flashlamp to generate a long effective laser light output pulse having an effective pulse duration of greater than 0.1 milliseconds, the long effective laser light pulse comprising a series of shorter-duration subpulses; and replacing at least some original dye solution in the resonant cavity with new dye solution while generating the long effective laser light pulse.

17. A method as described in claim 16, further comprising delivering the long effective laser light output pulse to tissue of a patient.

18. A method as described in claim 16, further comprising defining the effective pulse duration in response to the size of the targeted tissue of a patient.

19. A method as described in claim 16, further comprising generating the effective output laser light pulse having less than fifty Joules of energy.

* * * * *

UNITED STATES PATENT AND TRADEMARK OFFICE
CERTIFICATE OF CORRECTION

PATENT NO.    : 6,547,781 B1
DATED         : April 15, 2003
INVENTOR(S)   : Horace W. Furumoto It is certified that error appears in the above-identified patent and that said Letters Patent is hereby corrected as shown below:

<u>Title page,</u>
Item [73], Assignee, please delete "Cynsure" and insert -- Cynosure --.

Signed and Sealed this

Twenty-fifth Day of November, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,547,781 B1
DATED : April 15, 2003
INVENTOR(S) : Horace W. Furumoto It is certified that error appears in the above-identified patent and that said Letters Patent is hereby corrected as shown below:

<u>Title page,</u>
Item [73], Assignee, please delete "Cynsure" and insert -- Cynosure --.

<u>Column 11,</u>
Lines 56, 59 and 62, delete "1" and insert -- 2 --.

<u>Column 12,</u>
Lines 2, 6 and 9, delete "1" and insert -- 2 --.

Signed and Sealed this

Second Day of March, 2004

JON W. DUDAS
*Acting Director of the United States Patent and Trademark Office*